United States Patent
Barnell

(10) Patent No.: US 9,827,063 B1
(45) Date of Patent: Nov. 28, 2017

(54) HYBRID SEALED TRAY FOR LONG CATHETER DELIVERY SYSTEMS

(71) Applicant: Medtronic Vascular, Inc., Santa Rosa, CA (US)

(72) Inventor: Jeffrey Barnell, Santa Rosa, CA (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 0 days.

(21) Appl. No.: 15/277,509

(22) Filed: Sep. 27, 2016

Related U.S. Application Data

(60) Provisional application No. 62/359,049, filed on Jul. 6, 2016.

(51) Int. Cl.
- *A61B 19/02* (2006.01)
- *A61B 50/33* (2016.01)
- *A61F 2/95* (2013.01)
- *A61B 17/00* (2006.01)

(52) U.S. Cl.
CPC ........ *A61B 50/33* (2016.02); *A61B 17/00234* (2013.01); *A61F 2/95* (2013.01); *A61B 2017/00362* (2013.01)

(58) Field of Classification Search
CPC .............. A61B 50/38; A61B 17/00234; A61B 2017/00362; A61B 50/30; A61B 50/20; A61B 50/31; A61B 50/33; A61B 2050/005; A61B 2050/0065; A61F 2/95
USPC ................. 206/364, 363, 370, 438
See application file for complete search history.

(56) References Cited

U.S. PATENT DOCUMENTS

| | | | |
|---|---|---|---|
| 4,106,621 A * | 8/1978 | Sorenson | A61M 5/002 206/365 |
| 4,424,903 A * | 1/1984 | Knieper | G21F 9/02 206/525 |
| 4,943,284 A * | 7/1990 | Erlich | A61M 25/0111 206/365 |
| 5,096,055 A * | 3/1992 | Opper | B65D 5/5213 206/754 |
| 5,131,537 A * | 7/1992 | Gonzalez | B65D 75/326 206/364 |
| 5,181,612 A * | 1/1993 | Liu | A45C 7/0036 206/542 |
| 5,742,487 A | 4/1998 | Kobayshi et al. | |
| 6,428,515 B1 | 8/2002 | Bierman et al. | |

(Continued)

FOREIGN PATENT DOCUMENTS

CA              907570          8/1972

OTHER PUBLICATIONS

U.S. Appl. No. 62/359,049, of Jeffrey Barnell, titled "Hybrid Sealed Tray for Long Catheter Delivery Systems", filed Jul. 6, 2016.

(Continued)

Primary Examiner — Steven A. Reynolds

(57) ABSTRACT

A catheter delivery system package includes a tray, an extension tube coupled to the tray, an end cap sealing an end of the extension tube, and a lid coupled to the tray. The sealed rigid tray provides a highly robust sterile barrier, free of folds and abrasions. By eliminating compound folds, the possibility of failure of the catheter delivery system package is minimized. In addition, the catheter delivery system package has a reduced package volume. Further, the catheter delivery system package is 100% recyclable.

17 Claims, 7 Drawing Sheets

(56) References Cited

U.S. PATENT DOCUMENTS

| | | | |
|---|---|---|---|
| 6,896,141 B2* | 5/2005 | McMichael | A61B 50/33 206/370 |
| 7,160,270 B2 | 1/2007 | West et al. | |
| 7,261,205 B2* | 8/2007 | Cervantes | A61F 2/0095 206/363 |
| 2002/0130059 A1* | 9/2002 | Armijo | A61M 25/002 206/438 |
| 2005/0038453 A1 | 2/2005 | Raulerson | |
| 2005/0043715 A1* | 2/2005 | Nestenborg | A61M 25/002 604/544 |
| 2005/0252805 A1* | 11/2005 | Cervantes | A61F 2/0095 206/384 |
| 2009/0008279 A1* | 1/2009 | Tanghoej | A61M 25/002 206/364 |
| 2009/0306603 A1 | 12/2009 | Bierman et al. | |
| 2012/0305441 A1 | 12/2012 | Murray et al. | |
| 2013/0264226 A1* | 10/2013 | Prikril | A61B 17/06133 206/206 |
| 2014/0021074 A1* | 1/2014 | Kranz | B65D 81/268 206/204 |
| 2014/0110279 A1* | 4/2014 | Kruetzfeldt | A61F 2/2427 206/216 |

OTHER PUBLICATIONS

U.S. Appl. No. 15/277,537, of Jeffrey Barnell, titled "Biomatter Capture Mechanism and Method", filed Sep. 27, 2016.
U.S. Appl. No. 15/332,968, of Jeffrey Barnell et al., titled "Device Retention Mechanism and Method", filed Oct. 24, 2016.
U.S. Appl. No. 15/333,287, of John Gallagher, titled "Hinged Long Sealed Tray and Method", filed Oct. 25, 2016.
U.S. Appl. No. 15/333,317, of John Gallagher et al., titled "Slip Card for Long Sealed Trays and Method", filed Oct. 25, 2016.
PCT International Search Report corresponding to International Application No. PCT/US2017/040589, Sep. 27, 2017, 6 pages.

* cited by examiner

HYBRID SEALED TRAY FOR LONG CATHETER DELIVERY SYSTEMS

RELATED APPLICATIONS

This application claims the benefit of U.S. Provisional Application No. 62/359,049 filed on Jul. 6, 2016, entitled "HYBRID SEALED TRAY FOR LONG CATHETER DELIVERY SYSTEMS" of Jeffery Barnell, which is incorporated herein by reference in its entirety.

BACKGROUND

Field

The present application relates to packaging for an intra-vascular device and method. More particularly, the present application relates to packaging for a device for treatment of intra-vascular diseases and related methods.

Description of the Related Art

The current commercial catheter delivery product families utilize single or dual flexible pouches to create the sterile barrier. A separate thermoformed device tray secures the delivery system within the pouches. This approach is not ideal for devices of this length, total weight, and weight distribution. Vibration and shock during handling and delivery place significant stress on the barrier. The device tray can abrade the inner pouch. Repetitive flexing of the pouch especially at the confluence of multiple (compound) folds causes stress cracking and pin holes.

Given that each device may experience multiple delivery cycles before use, e.g., shipment back and forth, the sterile barrier margin of safety may be lower than preferred. The current pouch sterile barrier system has shown to be very challenging to develop and prove through validation testing.

Aseptic transfer difficulties arise from pouch-based sterile barriers. Nursing staff have demonstrated their challenges openings and presenting the device into the sterile field. The close proximity of the nonsterile pouch faces to the sterile surfaces makes the likelihood of contamination higher than ideal. The method used to open and present the device varies between nurses and facilities, some showing frustration and poor technique.

Pouch designs are inherently inefficient in regards to space and material. Cartons must be designed oversize, leading to excess material usage, inventory, and shipping overhead. Depending on the application, neither the pouches nor the tray can ultimately be recycled.

SUMMARY

A catheter delivery system package for housing a delivery system includes a tray, an extension tube coupled to the tray, an end cap sealing an end of the extension tube, and a lid coupled to the tray. The sealed rigid tray provides a highly robust sterile barrier, free of folds and abrasions typical of pouch based systems. By eliminating compound folds, the possibility of failure of the catheter delivery system sterile barrier is minimized. In addition, the catheter delivery system package has a reduced package volume. Further, unlike pouch based systems, the catheter delivery system package may be 100% recyclable depending on use.

Use of the catheter delivery system package better ensures no cross-contamination. Accordingly, sterile barrier performance is significantly improved. The entire procedure of using the catheter delivery system package to present and prepare the delivery system is easy and fast.

These and other features in accordance with various embodiments will be more readily apparent from the detailed description set forth below taken in conjunction with the accompanying drawings.

BRIEF DESCRIPTION OF DRAWINGS

Common reference numerals are used throughout the drawings and detailed description to indicate like elements.

DETAILED DESCRIPTION

As an overview, presented is a sealed rigid tray for a long catheter delivery system. The sealed rigid tray provides a highly robust sterile barrier, free of pouch folds and abrasions. With some limited constraints, one tray, lid, and carton serves a large variety of different delivery systems.

The aseptic presentation is not only easy and fast, but also allows the nurses to maintain better control of the delivery system, thus minimizing contamination. The tray is 100% recyclable, and also minimizes both packaging and shipping costs. The tray design is adaptable, making support for other long catheter delivery systems, e.g., Valiant EVO TAA products, possible.

Figure 1:
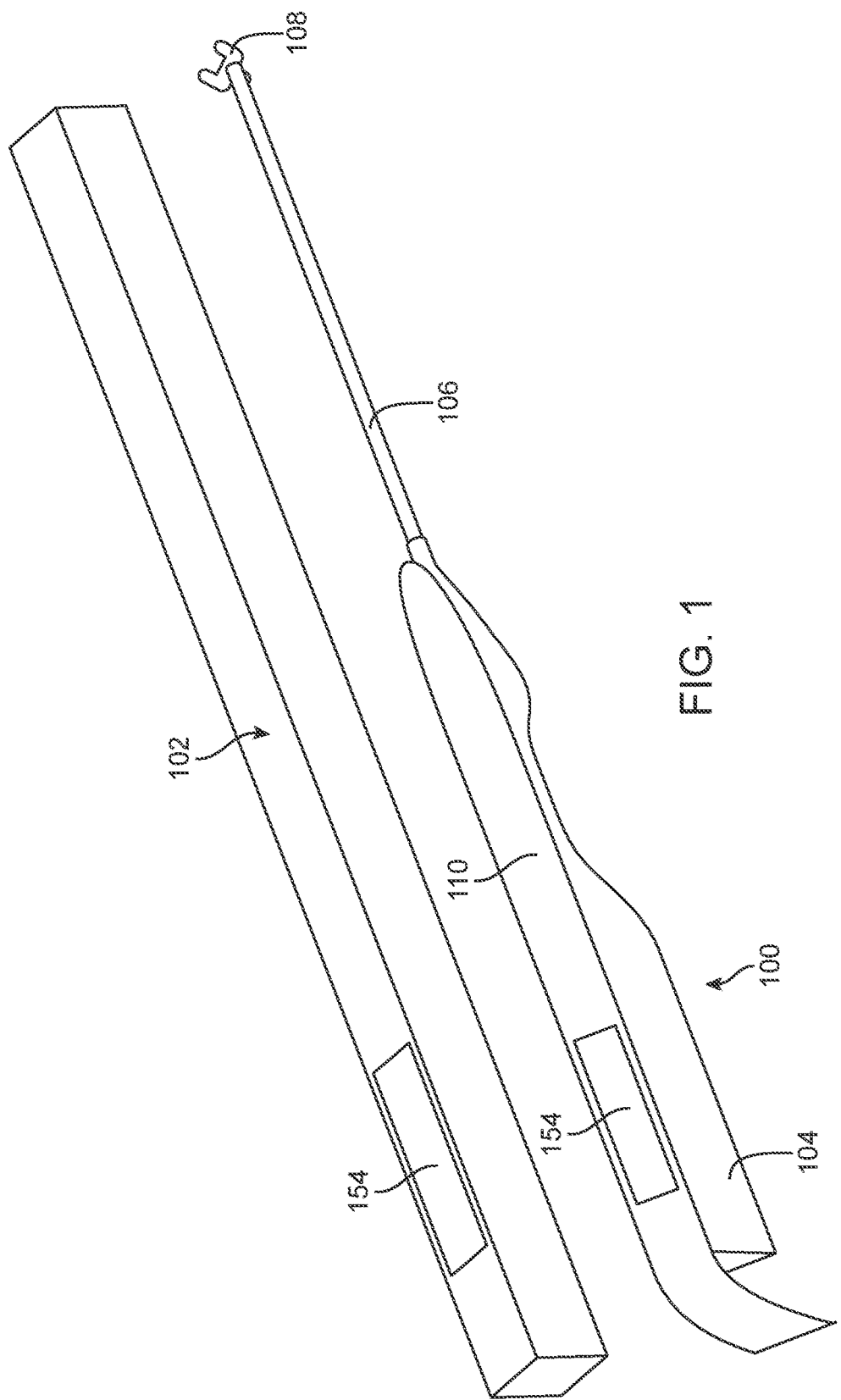
FIG. 1 is a perspective view of a catheter delivery system package and a shelf carton in accordance with one embodiment.
Figure 2:
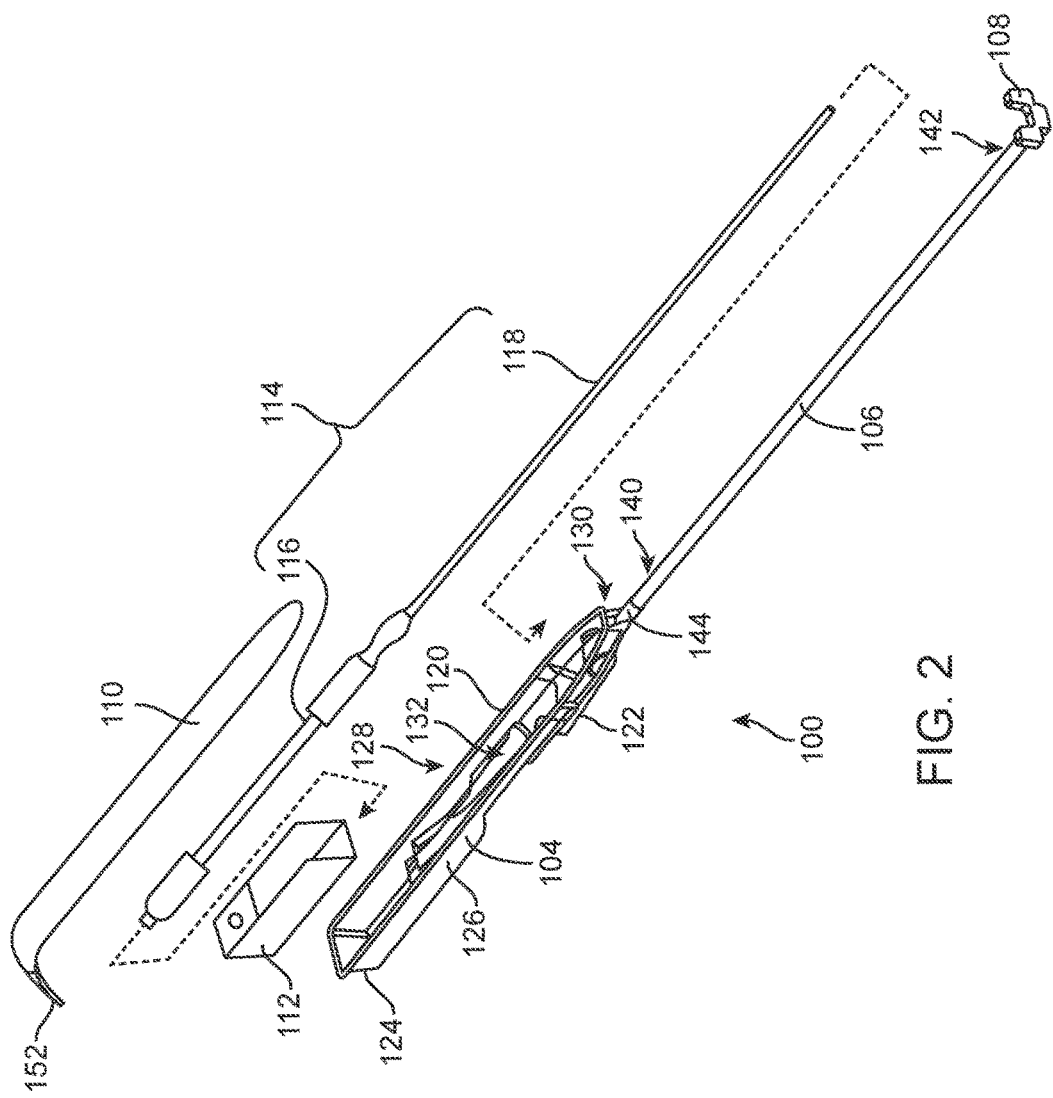
FIG. 2 is an exploded perspective view of the catheter delivery system package of FIG. 1 in accordance with one embodiment.
Figure 3:
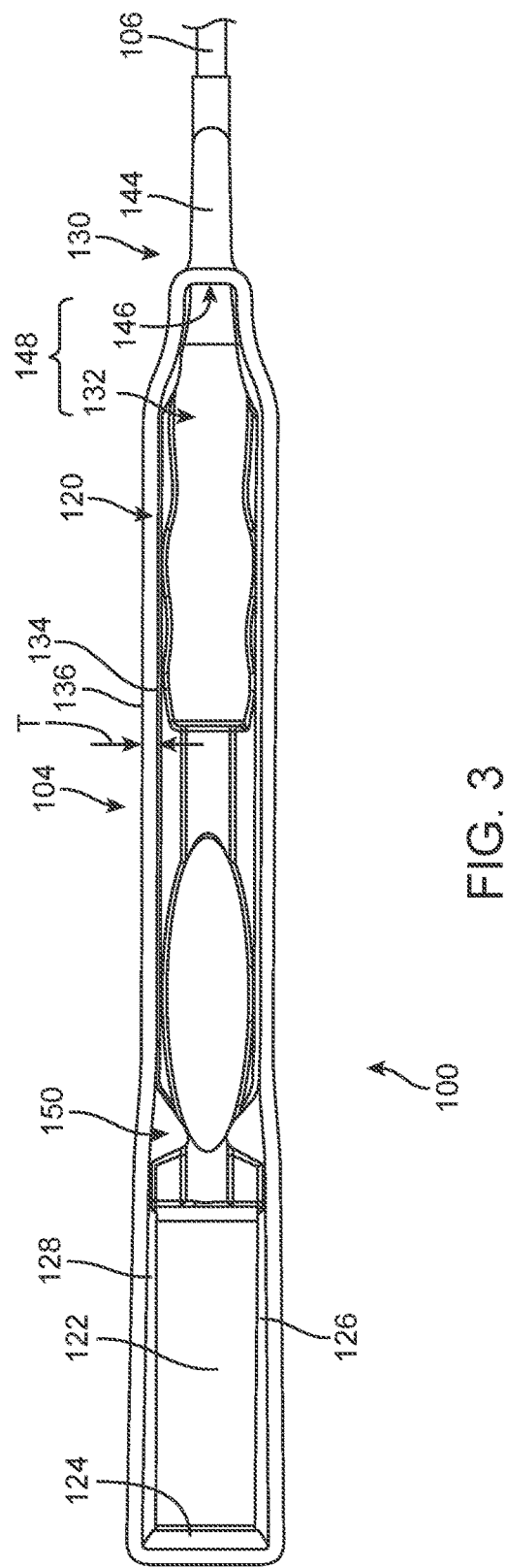
FIG. 3 is a top plan view of a tray of the catheter delivery system package of FIGS. 1 and 2 in accordance with one embodiment.
Figure 4:
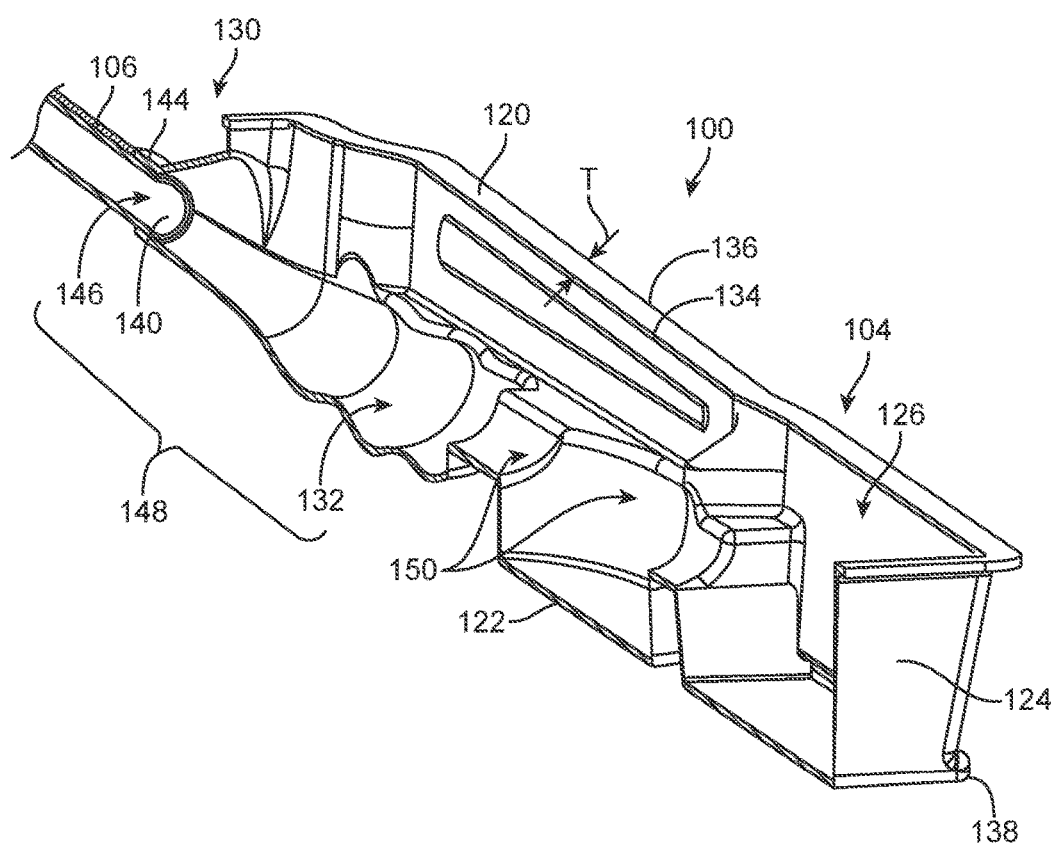
FIG. 4 is a perspective cross-sectional view of the tray of the catheter delivery system package of FIGS. 1 and 2 in accordance with one embodiment.

Now in more detail, FIG. 1 is a perspective view of a catheter delivery system package 100 and a shelf carton 102, sometimes called a box, in accordance with one embodiment. FIG. 2 is an exploded perspective view of catheter delivery system package 100 of FIG. 1 in accordance with one embodiment. FIG. 3 is a top plan view of a tray 104 of catheter delivery system package 100 of FIGS. 1 and 2 in accordance with one embodiment. FIG. 4 is a perspective cross-sectional view of tray 104 of catheter delivery system package 100 of FIGS. 1 and 2 in accordance with one embodiment.

Referring to FIGS. 1-4 together, catheter delivery system package 100 is transported or otherwise contained inside of shelf carton 102. Catheter delivery system package 100 includes tray 104, an extension tube 106, an end cap 108, a lid 110, and, optionally, a device removal assist card 112.

Catheter delivery system package 100 is a sterile barrier package for a delivery system 114. Delivery system 114 include a handle 116 and a protruding portion 118 protruding from handle 116. An example of delivery system 114 includes the Valiant EVO TAA system although other delivery systems are used in other embodiments.

In one embodiment, delivery system 114 includes one or more stents, grafts, stent-grafts, or other endoluminal devices for delivery and implantation within a patient. Protruding portion 118, e.g., having an outer sheath, is cylindrical in accordance with one embodiment and is configured to be inserted into a patient. Protruding portion 118 is not limited to a cylindrical member and can take various shapes and have various features in accordance with other embodiments.

Tray 104, sometimes called a common injection-molded body, is a hybrid sealed tray. Tray 104 includes an integral lid sealing flange 120 for sealing with lid 110. Tray 104 contains handle 116 of delivery system 114 therein. In various embodiments, tray 104 is formed using injection molding, blow molding, or thermoformed.

Tray 104 includes a bottom surface 122, a proximal end 124, sides 126, 128, and a distal end 130. Extension tube 106 is coupled to distal end 130 of tray 104. Sides 126, 128 and ends 124, 130 extend upward and away from bottom surface 122 to lid sealing flange 120. Sides 126, 128 extend opposite one another and between proximal end 124 and distal end 130. Similarly, proximal end 124 and distal end 130 extend opposite one another and between sides 126, 128.

As used herein, the distal end of delivery system 114 is identified as the end that is farthest from the operator (handle 116) while the proximal end of delivery system 114 is the end nearest the operator (handle 116). Similarly, the distal end of catheter delivery system package 100 is identified to the end that is farthest from tray 104 (handle 116) while the proximal end of catheter delivery system package 100 is the end nearest tray 104 (handle 116).

Lid sealing flange 120 is a continuous planar surface in accordance with this embodiment. Lid sealing flange 120 surrounds a tray cavity 132 defined by bottom surface 122, proximal end 124, sides 126, 128, and distal end 130. Lid sealing flange 120 includes a continuous inner edge 134 and a continuous outer edge 136. Lid sealing flange 120 has a uniform thickness T between inner edge 134 and outer edge 136.

In one embodiment, tray 104 includes a grasping feature 138, sometimes called a handle, to assist in grasping of tray 104. Grasping feature 138 is a protruding ridge at bottom surface 122. Grasping feature 138 allows the user to more firmly grasp tray 104 and prevents the user's hand from slipping off of tray 104, e.g., during removal of lid 110.

Hermetically welded to tray 104 is extension tube 106. Extension tube 106 is a simple, cylindrical, extruded tube although is injection molded in one embodiment. Extension tube 106 is sized for the length of the catheter, longer for thoracic and shorter for abdominal devices. Extension tube 106 is a closed profile such as a cylinder, an octagon, an oval, or a square in other embodiments. Extension tube 106 can taper end to end and/or include other functional features along its length, e.g., depending upon the application. Extension tube 106 contains protruding portion 118 therein. Extension tube 106 includes a proximal end 140 and a distal end 142.

Proximal end 140 of extension tube 106 is mounted to distal end 130 of tray 104. More particularly, distal end 130 of tray 104 includes a protruding extension tube mounting flange 144. Extension tube mounting flange 144 is a cylindrical tube in accordance with this embodiment. Proximal end 140 of extension tube 106 is slid inside of extension tube mounting flange 144 and then welded thereto.

End cap 108 hermetically seals distal end 142 of extension tube 106. An extension tube cavity 146 is defined by and within extension tube 106 and extends between proximal end 140 and distal end 142 of extension tube 106. Extension tube cavity 146 is in open communication with tray cavity 132.

Extension tube cavity 146 in combination with tray cavity 132 define a delivery system cavity 148 into which delivery system 114 is placed and sealed in a sterile condition. Generally, delivery system cavity 148 is a sterile sealed cavity defined by tray 104, extension tube 106, end cap 108 and lid 110.

More particularly, protruding portion 118 is slid into extension tube 106 though tray 104. Protruding portion 118 is slid into extension tube 106 until handle 116 is located within tray 104. Tray 104 includes various handle mounting features 150 such that handle 116 is pressed into tray 104 and compression fit, e.g., snapped, into handle mounting features 150. In one embodiment, device removal assist card 112 is inserting into tray 104 prior to or with handle 116. Generally, delivery system 114 is placed within delivery system cavity 148.

After delivery system 114 is placed in tray 104 and extension tube 106, the sterile barrier is created with the additional of lid 110, e.g., a sealed Tyvek or other flexible film lid. Lid 110 includes nonwoven high density polyethylene fibers in one embodiment. The sealing operation takes place on an industry-standard sealer, e.g., a thermal sealer, in one embodiment. Lid 110 includes a protruding tab 152 that protrudes proximally of tray 104. Protruding tab 152 assists in peeling of lid 110 from tray 104 as discussed further below. Generally, protruding tab 152 projects from proximal end 124 of tray 104.

Labels 154 are attached to lid 110, tray 104, and/or shelf carton 104 using an adhesive strip.

In one embodiment, High Density PolyEthylene (HDPE) is used for each component enabling reliable welding and recyclability. Each assembly is pressure tested for barrier integrity in one embodiment. By eliminating compound folds associated with pouch delivery systems, catheter delivery system package 100 has a greatly reduced chance of failure.

In addition, catheter delivery system package 100 and the associated carton 102 have reduced package volume as compared to use of flexible pouches. This creates an operational cost-savings opportunity. Reducing package volume allows more devices on the pallet, resulting in a lower shipping cost per device. Packaging material cost also decrease with the introduction of the simpler, small shelf carton and shipper.

Figure 5:
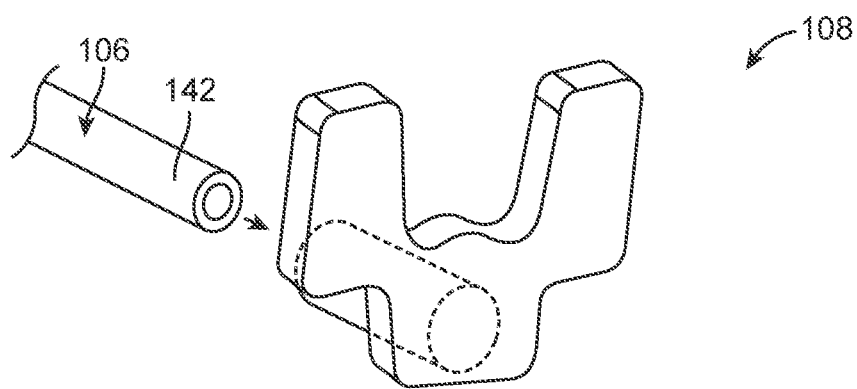
FIG. 5 is an exploded front view of an end cap and an extension tube of the catheter delivery system package of FIGS. 1 and 2 in accordance with one embodiment.
Figure 6:
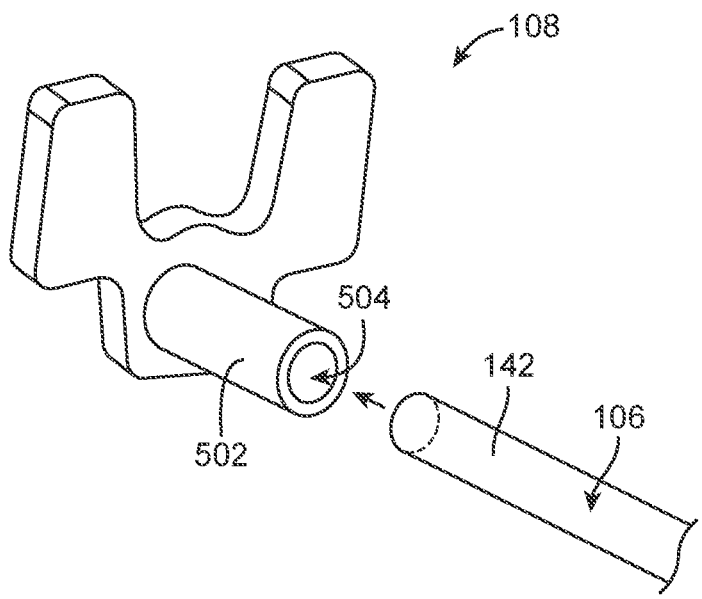
FIG. 6 is an exploded rear view of the end cap and the extension tube of FIG. 5 in accordance with one embodiment.

FIG. 5 is an exploded front view of end cap 108 and extension tube 106 of catheter delivery system package 100 of FIGS. 1 and 2 in accordance with one embodiment. FIG. 6 is an exploded rear view of end cap 108 and extension tube 106 of FIG. 5 in accordance with one embodiment.

As shown in FIGS. 5 and 6, end cap 108 is a solid end cap, e.g., for use with electronic beam (ebeam) sterilization. End cap 108 includes a protruding mold pin 502 in accordance with this embodiment. More particularly, mold pin 502 defines a sealed extension tube receiving cavity 504 therein. Distal end 142 of extension tube 106 is inserted into mold pin 502, and more particularly, into extension tube receiving cavity 504. Mold pin 502 is then welded to extension tube 106 to seal distal end 142 of extension tube 106.

Figure 7:
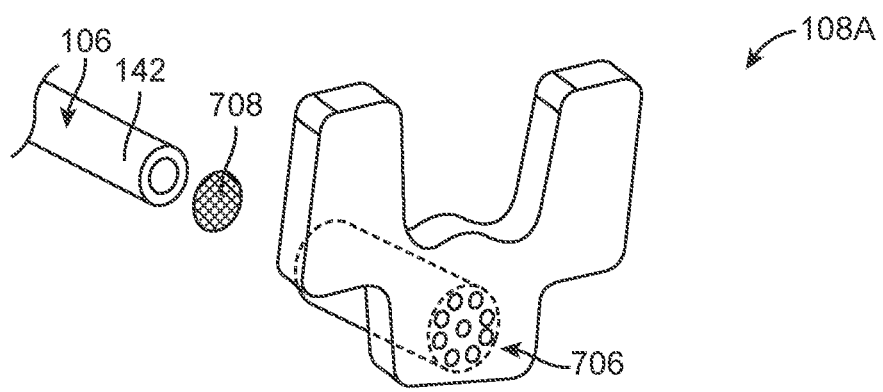
FIG. 7 is an exploded front view of an end cap and the extension tube of the catheter delivery system package of FIGS. 1 and 2 in accordance with another embodiment.
Figure 8:
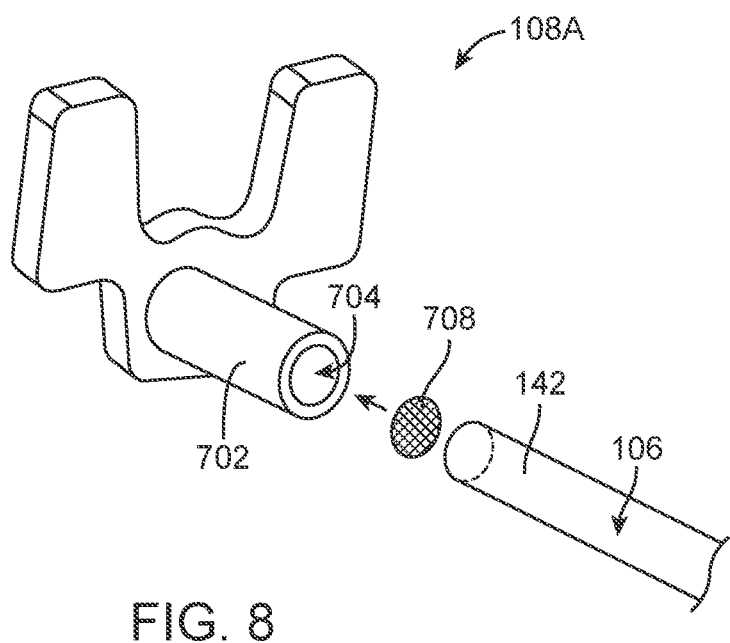
FIG. 8 is an exploded rear view of the end cap and the extension tube of FIG. 7 in accordance with one embodiment.

FIG. 7 is an exploded front view of an end cap 108A and extension tube 106 of catheter delivery system package 100 of FIGS. 1 and 2 in accordance with another embodiment. FIG. 8 is an exploded rear view of end cap 108A and extension tube 106 of FIG. 7 in accordance with one embodiment. As shown in FIGS. 7 and 8, end cap 108A has openings 706 therein to accommodate passing of ethylene oxide (EtO) for EtO sterilization. A filter 708, e.g., polyester, is situated over the openings 706 to allow ethylene oxide to pass yet to block pathogens.

End cap 108A includes a protruding mold pin 702 in accordance with this embodiment. More particularly, mold pin 702 defines an extension tube receiving cavity 704 therein. Filter 708 is located within extension tube receiving cavity 704 and covers openings 706 which extend to extension tube receiving cavity 704. Distal end 142 of extension tube 106 is inserted into mold pin 702, and more particularly, into extension tube receiving cavity 704. In one embodiment, filter 708 is inserted first and then distal end 142 of extension tube 106 is inserted to compress and secure filter 708 between end cap 108A and extension tube 106. Mold pin 702 is then welded to extension tube 106 to seal distal end 142 of extension tube 106.

Although FIGS. 5-8 illustrate various embodiments, given the appropriate materials, design, and venting, multiple forms of sterilization are supported in addition to EtO and ebeam sterilization such as steam and gamma sterilization in other embodiments.

Figure 9:
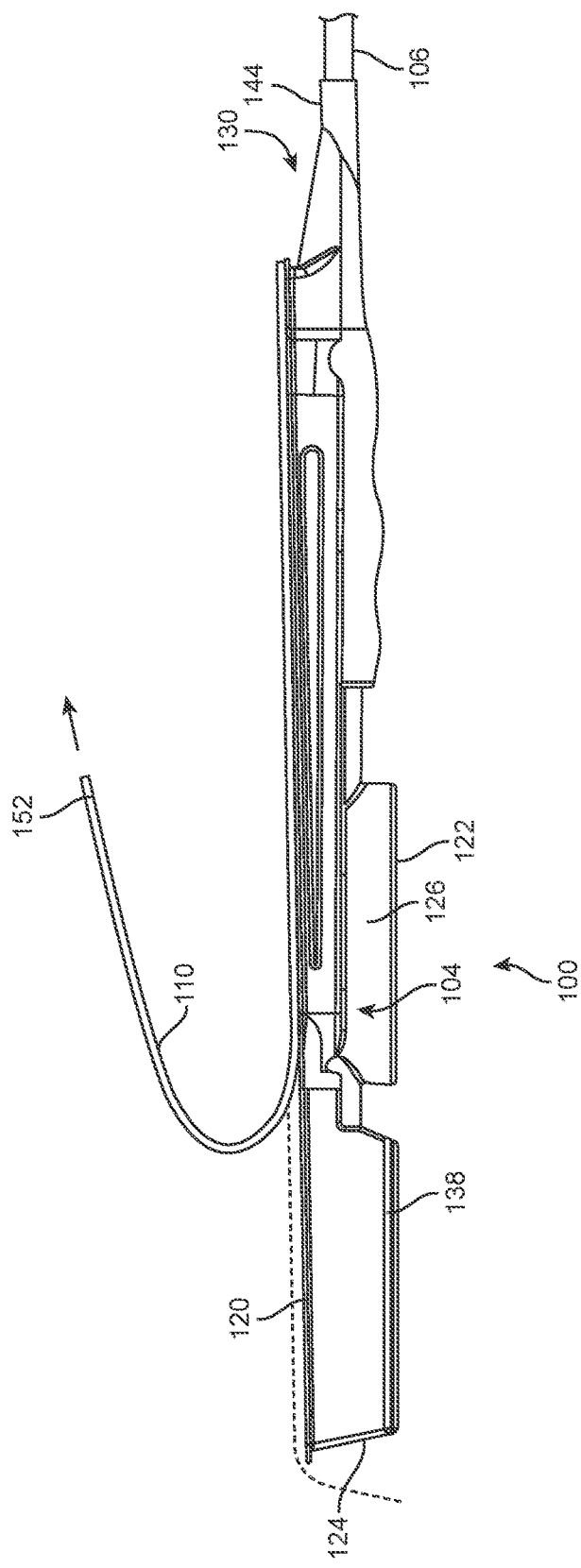
FIG. 9 is a side perspective view of the catheter delivery system package of FIGS. 1 and 2 during opening in accordance with one embodiment.

FIG. 9 is a side perspective view of catheter delivery system package 100 of FIGS. 1 and 2 during opening in accordance with one embodiment. As illustrated in FIG. 9, once out of the shelf carton 102 (see FIG. 1), the circulating nurse or other user holds tray 104, e.g., with the assistance of grasping feature 138. This nurse then grasps protruding tab 152 of lid 110 and peels lid 110 from tray 104 as illustrated in FIG. 9 to expose the proximal end of the delivery system 114 and more particularly handle 116.

With one hand, the scrub nurse or other staff member in the sterile field pulls a lifting tab of device removal assist card 112 (illustrated in FIG. 2). Device removal assist card 112 is located between delivery system 114 and tray 104. Accordingly, pulling of the lifting tab of device removal assist card 112 raises handle 116 of delivery system 114 from tray 104. In one embodiment, device removal assist card 112 projects over lid sealing flange 120 thereby isolating delivery system 114 from lid sealing flange 120. The scrub nurse or other user then pulls delivery system 114 from tray 104 with the other hand.

In another embodiment, catheter delivery system package 100 does not include device removal assist card 112. In accordance with this embodiment, after lid 110 is peeled back, the scrub nurse or other user reaches into tray 104 and directly grabs handle 116 of delivery system 114. The scrub nurse or other user then pulls delivery system 114 from tray 104.

Use of catheter delivery system package 100 better ensures no cross-contamination. Accordingly, sterile barrier performance is significantly improved, where sterile barrier performance is a characteristic of the closed package 100 before lid 110 is peel off in one embodiment. The entire procedure can be completed in a short time, e.g., 8-10 seconds or less. This is in contrast to removal from a pouch which can take 60 seconds or longer.

In addition, users, e.g., customers, like the ease and speed in which catheter delivery system package 100 presents and prepares delivery system 114. Further, the catheter delivery system package 100 and carton 102 are 100% recyclable in one embodiment.

This disclosure provides exemplary embodiments. The scope is not limited by these exemplary embodiments. Numerous variations, whether explicitly provided for by the specification or implied by the specification or not, such as variations in structure, dimension, type of material and manufacturing process may be implemented by one of skill in the art in view of this disclosure.

What is claimed is:

1. A catheter delivery system package comprising:
    a tray, where a distal end of the tray includes an extension tube mounting flange;
    an extension tube coupled to the tray, a proximal end of the extension tube being inside of the extension tube mounting flange;
    an end cap sealing an end of the extension tube; and
    a lid coupled to the tray, wherein only the proximal end of the extension tube is coupled to the tray and the end cap is coupled to only a distal end of the extension tube.

2. The catheter delivery system package of claim 1 wherein the tray comprises a lid sealing flange.

3. The catheter delivery system package of claim 2 wherein the lid sealing flange is planar.

4. The catheter delivery system package of claim 3 wherein the lid sealing flange comprise a continuous inner edge.

5. The catheter delivery system package of claim 4 wherein the lid sealing flange further comprises a continuous outer edge.

6. The catheter delivery system package of claim 5 wherein the lid sealing flange has a uniform thickness between the inner edge and the outer edge.

7. The catheter delivery system package of claim 1 wherein the lid comprises nonwoven high density polyethylene fibers.

8. The catheter delivery system package of claim 1 wherein the lid is thermally sealed to the tray.

9. The catheter delivery system package of claim 1 wherein the lid comprises a tab projecting from a proximal end of the tray.

10. The catheter delivery system package of claim 1 wherein the end cap comprises a mold pin comprising a sealed tube defining a receiving cavity therein.

11. The catheter delivery system package of claim 10 wherein the end cap is solid.

12. A catheter delivery system package comprising:
    a tray;
    an extension tube coupled to the tray;
    an end cap sealing an end of the extension tube; and
    a lid coupled to the tray, wherein the end cap comprises openings therein, the catheter delivery system package further comprising a filter covering the openings.

13. The catheter delivery system package of claim 1 further comprising a device removal assist card located within a cavity defined by the tray and the lid.

14. A catheter delivery system assembly comprising:
    a catheter delivery system package comprising a sealed cavity defined by a tray, an extension tube, an end cap, and a lid, where a distal end of the tray includes an extension tube mounting flange, a proximal end of the extension tube being inside of the extension tube mounting flange, wherein only the proximal end of the extension tube is coupled to the tray and the end cap is coupled to only a distal end of the extension tube; and
    a delivery system within the sealed cavity.

15. The catheter delivery system assembly of claim 14 further comprising a device removal assist card located within the sealed cavity between the delivery system and the tray.

16. The catheter delivery system assembly of claim 15 wherein the tray comprises a grasping feature.

17. The catheter delivery system package of claim 1 wherein the proximal end of the extension tube is welded to the extension tube mounting flange.

\* \* \* \* \*